US006696498B2

(12) United States Patent
Santoro et al.

(10) Patent No.: US 6,696,498 B2
(45) Date of Patent: *Feb. 24, 2004

(54) 2-CYCLOPENTEN-1-ONE AND ITS DERIVATIVES AS INHIBITORS OF THE NF-KB FACTOR

(75) Inventors: Maria Gabriella Santoro, Avellino (IT); Antonio Rossi, Colledimacine (IT); Giuliano Elia, Palestrina (IT)

(73) Assignee: Consiglio Nazionale Della Richerche, Rome (IT)

( * ) Notice: Subject to any disclaimer, the term of this patent is extended or adjusted under 35 U.S.C. 154(b) by 13 days.

This patent is subject to a terminal disclaimer.

(21) Appl. No.: 10/142,813

(22) Filed: May 10, 2002

(65) Prior Publication Data

US 2002/0137800 A1 Sep. 26, 2002

Related U.S. Application Data

(63) Continuation of application No. 09/319,743, filed as application No. PCT/EP97/06930 on Dec. 11, 1997, now Pat. No. 6,392,100.

(30) Foreign Application Priority Data

Dec. 13, 1996 (IT) ........................................ RM96A0867

(51) Int. Cl.⁷ ........................ A01N 35/00; C07C 49/105
(52) U.S. Cl. ........................ 514/690; 568/379; 568/380
(58) Field of Search ................... 568/379, 380; 514/690

(56) References Cited

U.S. PATENT DOCUMENTS

| | | | |
|---|---|---|---|
| 4,711,895 A | 12/1987 | Hazato et al. | |
| 4,954,519 A | 9/1990 | Powers et al. | |
| 5,116,869 A | 5/1992 | Sugiura et al. | |
| 5,216,183 A | 6/1993 | Sugiura et al. | |
| 5,338,844 A | 8/1994 | Sugiura et al. | |
| 5,684,205 A | 11/1997 | Norman et al. | |
| 6,087,401 A | 7/2000 | Koyama et al. | |
| 6,111,145 A | 8/2000 | Kobayashi et al. | |
| 6,180,681 B1 | 1/2001 | Amici et al. | |
| 6,410,516 B1 | 6/2002 | Baltimore et al. | |

FOREIGN PATENT DOCUMENTS

| | | | |
|---|---|---|---|
| DE | 4311835 | | 10/1994 |
| EP | 0131441 | * | 7/1984 |
| JP | 60097926 | * | 5/1985 |
| JP | 61047437 | * | 3/1986 |
| JP | 62-44 | | 1/1987 |
| JP | 63072672 | * | 4/1988 |
| JP | 6209258 | * | 7/1994 |
| JP | 7-233142 | | 9/1995 |
| JP | 9-169780 | | 6/1997 |
| WO | WO 97/48389 | | 12/1997 |
| WO | WO 98/25593 | | 6/1998 |
| WO | WO 98/41196 | | 9/1998 |
| WO | WO 99/01117 | | 1/1999 |

OTHER PUBLICATIONS

Atsmon et al. Conjugation of 9–deoxy–delta 9,delta 12(E)–prostaglandin D2 with intracellular glutathione and enhancement of its antiproliferative activity by glutathione depletion. Cancer Res. 1990 Mar 15;50(6):1879–85.
Fukushima M. Prostaglandin J2—anti–tumour and anti–viral activities and the mechanisms involved. Eicosanoids. 1990;3(4):189–99. Review.
Fukushima et al. Mode of action of antitumor prostaglandins. Proceedings of AACR (Seventy–seventh annual meeting of the American Association for Cancer Research) vol. 27, Mar. 1986, pp 274, abstract # 1085.
Fukushima and Kato, In *Icosanoids and Cancer*, Thaler–Dao, de Paulet and Paoletti eds), Raven Press 1984, pp 275–278.
Fukushima et al. Prostaglandin A and J: antitumor and antiviral prostaglandins. Adv Prostaglandin Thromboxane Leukot Res. 1989;19:415–8.
Goodwin J.S. (Editor) *Prostaglandins and Immunity*. Martinus Nijhoff Publishing, Boston/Dordrecht/Lancaster.
Ham et al. The reaction of PGA1 with sulfhydryl groups; a component in the binding of A–type prostaglandins to proteins. Prostaglandins. 1975 Aug;10(2):217–29.
Honda et al. Structure requirements for antiproliferative and cytotoxic activities of marine coral prostanoids from the Japanese stolonifer Clavularia viridis against human myeloid leukemia cells in culture. Prostaglandins. 1988 Nov;36(5):621–30.
Honn et al. Prostaglandin analogs as inhibitors of tumor cell DNA synthesis. Proc Soc Exp Biol Med. 1981 Apr;166(4):562–7.
Honn et al. Requirement of a reactive alpha, beta–unsaturated carbonyl for inhibition of tumor growth and induction of differentiation by "A" series prostaglandins. Biochem Biophys Res Commun. 1985 May 31;129(1):34–40.
Hughes–Fulford et al. Inhibition of DNA synthesis and cell cycle by prostaglandins independent of cyclic AMP. In *Advances in Prostaglandin, Thromboxane, and Leukotriene Research*. Hayaishi et al. Eds., Raven Press 1985, New York, vol. 15, pp 401–404.
Kato et al. Antitumor activity of delta 7–prostaglandin A1 and delta 12–prostaglandin J2 in vitro and in vivo. Cancer Res. 1986 Jul;46(7):3538–42.
Khan et al. Preferential binding of growth inhibitory prostaglandins by the target protein of a carcinogen. Proc Natl Acad Sci U S A. 1990 Dec;87(23):9401–5.

(List continued on next page.)

Primary Examiner—Johann Richter
Assistant Examiner—Sikarl A. Witherspoon
(74) Attorney, Agent, or Firm—Pennie & Edmonds LLP

(57) ABSTRACT

2-Cyclopenten-1-one and its derivatives comprising the cyclopentenone nucleus as inhibitors of the NF-kB factor, with anti-inflammatory, anti-proliferative-immunosuppressive, cytoprotective and antiviral activity, the substituents being selected among the ones which do not affect NF-kB inhibitory activity.

22 Claims, 1 Drawing Sheet

OTHER PUBLICATIONS

Narumiya et al. delta 12–Prostaglandin J2, an ultimate metabolite of prostaglandin D2 exerting cell growth inhibition. Biochem Biophys Res Commun. 1985 Mar 29;127(3):739–45.

Narumiya, Fukushima and Hayaishi, In *Prostaglandins, Leukotrienes and Cancer*, vol. 4 ( Honn and Marnett eds) Martinus–Nijhoff Press, 1985.

Narumiya et al. Site and mechanism of growth inhibition by prostaglandins. I. Active transport and intracellular accumulation of cyclopentenone prostaglandins, a reaction leading to growth inhibition. J Pharmacol Exp Ther. 1986 Nov;239(2):500–5.

Narumiya and Fukushima, Cyclopetenone prostaglandin: anti–proliferative and anti–viral actions and their molecular mechanism. 1$^{st}$ International Conf. Detroit, Eicosanoids and Bioactive Lipids in Cancer & Radiation Injury 1989.

Ohno et al. Metabolic dehydration of prostaglandin E2 and cellular uptake of the dehydration product: correlation with prostaglandin E2–induced growth inhibition. Biochem Biophys Res Commun. Sep. 14, 1986;139(2):808–15.

Osato et al. Experimental chemotherapy of cancer in rat with citral–combinations. Gann, 1953; 44:348–53 (in Japanese with English abstract).

Santoro et al. Inhibition of tumour growth in vivo and in vitro by prostaglandin E. Nature. Oct. 28, 1976;263(5580):777–9.

Santoro et al. Prostaglandin A1 induces the synthesis of a new protein in cultured AGMK cells. Biochem Biophys Res Commun. Aug. 31, 1982;107(4):1179–84.

Santoro et al. Inhibition of virus protein glycosylation as the mechanism of the antiviral action of prostaglandin A in Sendai virus–infected cells. J Gen Virol. 1989 Apr;70 ( Pt 4):789–800.

Santoro et al. Inhibition of B–16 melanoma growth in vivo by a synthetic analog of prostaglandin E2. Cancer Res. 1977 Oct;37(10):3774–9.

Santoro et al. Inhibition of Friend erythroleukaemia–cell tumours in vivo by a synthetic analogue of prostaglandin E2. Br J Cancer. 1979 Apr;39(4):408–13.

Santoro et al. Prostaglandin A1 induces differentiation in Friend erythroleukemia cells. Prostaglandins. 1979 May;17(5):719–27.

Santoro, M.G. Involvement of protein synthesis in the antiproliferative and the antiviral action of prostaglandins. In *Prostaglandins in Cancer Research*. Garaci et al. Eds., 1987 Springer–Verlag pp 97–114.

Santoro et al. Modulation of the growth of a human erythroleukemic cell line (K562) by prostaglandins: antiproliferative action of prostaglandin A. Cancer Res. 1986 Dec;46(12 Pt 1):6073–7.

Santoro et al. PGJ2, a new antiviral prostaglandin: inhibition of Sendai virus replication and alteration of virus protein synthesis. J Gen Virol. 1987 Apr;68 (Pt 4):1153–8.

Sugiura et al. Synthesis of new antineoplastic prostaglandins. Chem Pharm Bull (Tokyo). 1984 Nov; 32(11):4658–61.

Amici et al., 1993, "Induction of Thermotolerance by Prostaglandin A in Human Cells", Exp. Cell Res. 207:230–234.

Amici et al., 1992, "Antiproliferative Prostaglandins Activate Heat Shock Transcription Factor", Proc. Natl. Acad. Sci. USA 89:6227–6231.

Amici et al., 1994, "Selective Inhibition of Virus Protein Synthesis by Prostaglandin A$_1$: a Translational Block Associated with HSP70 Synthesis", J. Virol. 68:6890–6899.

Amici et al. 1995, "Aspirin enhances thermotolerance in human erythroleukemic cells: an effect associated with the modulation of the heat shock response". Cancer Res. 55(19):4452–7.

Anggard et al. "Essential fatty acids and prostaglandins—an introductory overview." in *Therapeutic Applications of Prostaglandins*. pp. 1–14, Vane & O'Grady Eds. Edword Arnold, London.

Baeuerle et al. 1994, "Function and activation of NF–kappa B in the immune system". Annu Rev Immunol. 12:151–79. Review.

Baldwin AS Jr. 1996, "The NF–kappa B and I kappa B proteins: new discoveries and insights". Annu Rev Immunol. 14:649–83. Review.

Becker et al. 1995, "Analysis of proteins that interact with the IL–2 regulatory region in patients with rheumatic diseases". Clin Exp Immunol. 99(3):325–30.

Breithaupt et al., 1996, "The Suppression of T Cell Function and NFκB Expression by Serine Protease Inhibitors Is Blocked by N–Acetylcysteine", Cell. Immunol. 173:124–130.

Centers for Disease Control and Prevention, 1996, "Prevention and Control of Influenza: Recommendations of the Advisory Committee on Immunization Practices", Morbid. Mortal. Weekly Rep. 45(RR–5):1–24.

Chen et al., 1995, "Dependence and Reversal of Nitric Oxide Production of NF–κB in Silica and Lipopolysaccharide–Induced Macrophages", Biochem. Biophys. Res. Comm. 214:839–846.

Conant et al., 1996, "Extracellular Human Immunodeficiency Virus Type 1 Tat Protein Is Associated with an Increase in both NF–κB Binding and Protein Kinase C Activity in Primary Human Astrocytes", J. Virol. 70:1384–1389.

Conti et al., 1999, "Antiviral Effect of Hyperthermic Treatment in Rhinovirus Infection", Antimicrob. Agents Chemother. 43:822–829.

Denko et al., 1997, "Protease inhibitor TPCK Represses Ha–ras (Val12) Transformation and Nuclear Factor κB Actrivation", Int. J. Oncol. 10:895–900.

Elia et al., 1999, Induction of Ferritin and Heat Shock Proteins by Prostaglandin A$_1$ in Human Monocytes. Evidence for Transcriptional and Post–Transcriptional Regulation 264:736–745.

Feige and van Eden,, 1996, "Infection, Autoimmunity and Autoimmune Disease", in: *Stress–Inducible Cellular Responses*, Feige et al, eds., Birkhäuser Verlag, Basel, pp. 359–373.

Finco et al., 1994, "Inducible Phosphorylation of IκBα Is Not Sufficient for Its Dissociation from NF–κB and Is Inhibited by Protease Inhibitors", Proc. Natl. Acad. Sci USA 91:11884–11888.

Fukushima et al., 1982, "9–Deoxy–Δ$^9$–Prostaglandin D$_2$, a Prostaglandin D$_2$ Derivative with Potent Antineoplastic and Weak Smooth Muscle–Contracting Activities", Biochem. Biophys. Res. Comm. 109:626–633.

Grimm S. and Baeuerle PA.., 1993 "The inducible transcription factor NF–kappa B: structure–function relationship of its protein subunits." Biochem J. 290 ( Pt 2):297–308. Review.

Guesdon et al., 1995, "Interleukin 1–Induced Phosphorylation of MAD3, the Major Inhibitor of Nuclear Factor κB of HeLa Cells. Interference in Signalling by the Proteinase Inhibitors 2,4–Dichloroisocoumarin and Tosylphenylalanyl Chloromethylketone", Biochem. J. 307:287–295.

Halazy et al., 1992, "Synthesis and Antiviral Properties of New Cycloalkanol Derivatives of Guanine", Nucleosides & Nucleotides 11:1595–1606.

Hanss et al. "Metabolism and toxicology of the prostaglandins". In *Therapeutic Applications of Prostaglandins*. pp. 37–47, Vane & O'Grady Eds. Edword Arnold, London.

Hungate et al., 1991, "Synthesis of Cyclic Valine Analogs", Tetrahed. Lett. 32:6851–6854.

Lee et al., 1978, "Antitumor Agents. 32. Synthesis and Antitumor Activity of Cyclopentenone Derivatives Related to Helenalin", J. Med. Chem. 21:819–822.

Lenardo MJ & Baltimore D. 1989, "NF–kappa B: a pleiotropic mediator of inducible and tissue–specific gene control". Cell. 58(2):227–9. Review.

Lindquist et al., 1988, "The Heat–Shock Proteins", Annu. Rev. Genet. 22:631–677.

Liu et al., 1996, "Attenuated Heat Shock Transcriptional Response in Aging: Molecular Mechanism and Implication in the Biology of Aging", in: *Stress–Inducible Cellular Responses*, Feige et al., eds., Birkhäuser Verlag, Basel, pp. 393–408.

Marber et al., 1994, "Myocardial Protection after Whole Body Heat Stress in the Rabbit Is Dependent on Metabolic Substrate and Is Related to the Amount of the Inducible 70kD Heat Stress Protein", J. Clin. Invest. 93:1087–1094.

Maria et al., 1995, "Gastric Cytoprotective Activity of 2–Cyclopenten–1–one and Related Compounds", Biol. Pharm. Bull. 18:1784–1786.

Morimoto et al., 1992, "Transcriptional Regulation of Heat Shock Genes. A Paradigm for Inducible Genomic Responses", J. Biol. Chem. 267:21987–21990.

Morimoto and Santoro, 1998, "Stress–Inducible Responses and Heat Shock Proteins: New Pharmacologic Targets for Cytoprotection"., Nature Biotechnol. 16:833–838.

Myers et al., 1996, "An improved preparation of highly enantiomerically enriched (R)–(+)–4–tert–butyldimethylsiloxy–2–cyclopenten–1–one". Tetrahedron Lett. 37(18):3083–86.

Nakagawa et al., 1982, "Effect of Proteinase Inhibitors Having Anti–Inflammatory Activity on Gelatinase, Elastase and Cathepsin G Isolated from Rat Polymorphonuclear Leukocytes", J. Pharm. Dyn. 5:319–327.

Negishi et al., 1995, "Biological Actions of $\Delta^{12}$–prostaglandin $J_2$", J. Lipid Mediators Cell Signalling 12: 443–8.

Parker et al., 1995, "Antiviral Effect of Cyclopentenone Prostaglandins on Vesicular Stomatitis Virus Replication", Antiviral Res. 26:83–96.

Pica et al., 1993, "Inhibition of Vesicular Stomatitis Virus Replication by $\Delta^{12}$–Prostaglandin $J_2$ is Regulated at Two Separate Levels and Is Associated with Induction of Stress Protein Synthesis", Antiviral Res. 20:193–208.

Pica et al., 1996, "Effect of Combined αIFN and Prostaglandin $A_1$ Treatment on Vesicular Stomatitis Virus Replication and Heat Shock Protein Synthesis in Epithelial Cells", Antiviral Res. 29:187–198.

Polla and Cossarizza, 1996, "Stress Proteins in Inflammation", in: *Stress–Inducible Cellular Responses*, Feige et al., eds., Birkhäuser Verlag, Basel, pp. 375–391.

Rossi et al. 1996, 2–Cyclopenten–1–one, a new inducer of heat shock protein 70 with antiviral activity. J Biol Chem. 271(50):32192–6.

Rossi et al. 1996, "HSF Induction by cyclopentenone prostaglandins prevents NF–KB activation in human cells: Inplications in the control of virus infection". May 1–5, p 255.

Rossi et al. 1997, Inhibition of nuclear factor kappa B by prostaglandin A1: an effect associated with heat shock transcription factor activation. Proc Natl Acad Sci U S A. 94(2):746–50.

Rossi et al., 2000, "Anti–Inflammatory Cyclopentenone Prostaglandins are Direct Inhibitors of IΔB Kinase", Nature 403:103–108.

Rossi et al., 1995, "Induction by Prostaglandin $A_1$ of Haem Oxygenase in Myoblastic Cells: an Effect Independent of Expression of the 70 kDa Heat Shock Protein", Biochem. J. 308:455–463.

Rozera et al. 1996, "Inhibition of HIV–1 replication by cyclopentenone prostaglandins in acutely infected human cells. Evidence for a transcriptional block". J Clin Invest. 97(8):1795–803.

Salminen et al. 1995, "Alteration of transcription factor binding activities in the ischemic rat brain". Biochem Biophys Res Commun. 212(3):939–44.

Santoro et al. 1989, "Prostaglandins with antiproliferative activity induce the synthesis of a heat shock protein in human cells". Proc Natl Acad Sci U S A. 86(21):8407–11.

Santoro, 1996, "Viral Infection", in: *Stress–Inducible Cellular Responses*, Feige et al., eds., Birkhäuser Verlag, Basel, pp. 337–357.

Santoro, 2000, "Heat Shock Factors and the Control of the Stress Response", Biochem. Pharmacol. 59:55–63.

Santoro and Roberts, 1999, "Search for Novel Cytoprotective and Antiviral Prostanoids", Drug News Perspect 12:395–400.

Santoro, 1994, "Heat Shock Proteins and Virus Replication: HSP70s as Mediators of the Antiviral Effects of Prostaglandins", Experientia 50:1039–1047.

Santoro, 1997, "Antiviral Activity of Cyclopentenone Prostanoids", Trends Microbiol. 5:276–281.

Santoro et al., 1988, "Antiviral Activity of a Synthetic Analog of Prostaglandin A in Mice Infected with Influenza A Virus", Arch. Virol. 99:89–100.

Schnebli, 1974, "Growth Inhibition of Tumor Cells by Protease Inhibitors: Consideration of the Mechanisms Involved", Cold Spring Harbor Conferences on Cell Proliferation, vol. 1, Control of Proliferation in Animal Cells Clarkson et al., eds., Cold Spring Harbor Laboratory Press, CSH, NY.

Superti et al., 1998, "Inhibition of Rotavirus Replication by Prostaglandin A: Evidence for a Block of Virus Maturation", J. Infect. Dis. 178:564–568.

Thanos et al. 1995, "NF–kappa B: a lesson in family values". Cell. 80(4):529–32. Review.

Wu et al., 1996, "Inhibition of NF–κB/Rel Induces Apoptosis of Murine B Cells", EMBO J. 15:4682–4690.

Yang and Schnellmann, 1996, "Proteinases in Renal Cell Death", J. Toxicol. Environ. Health 48:319–332.

Zabel et al. 1991 "DNA binding of purified transcription factor NF–kappa B. Affinity, specificity, Zn2+ dependence, and differential half–site recognition." J Biol Chem. 266(1):252–60.

Zhirnov et al., 1986, "Alphavirus Replication in Cultured Cells and Infected Animals Is Inhibited by Antiproteinase Agents", Antiviral Res. 6:255–265.

\* cited by examiner

ABCUS 6,696,498 B2

2-CYCLOPENTEN-1-ONE AND ITS DERIVATIVES AS INHIBITORS OF THE NF-KB FACTOR

This is a continuation of United States application Ser. No. 09/319,743, filed Jun. 10, 1999, now U.S. Pat. No. 6,392,100 which is a 371 of PCT/EP97/06930 filed Dec. 11, 1997, which is herein Incorporated by reference in its entirety.

FIELD OF INVENTION

The present invention relates to 2-cyclopenten-1-one and its derivatives as inhibitors of the transcription factor Nuclear Factor-kappaB (NF-kB). In particular the invention relates to 2-cyclopenten-1-one and its derivatives comprising the cyclopentenone nucleus as inhibitors of the NF-kB factor with anti-inflammatory, anti-proliferative, immuno-suppressive, cytoprotective and antiviral activity.

BACKGROUND OF THE INVENTION

NF-kB (Nuclear Factor-κB) is an eucariotic transcription factor of the rel family, which is normally located in the cytoplasm in an inactive complex, whose predominant form is a heterodimer composed of p50 and p65 subunits, bound to inhibitory proteins of the IkB family, usually IkB-alpha (D. Thanos and T. Maniatis, and Cell 80:529–532, 1995).

NF-kB is activated in response to different stimuli, among which phorbol esters, inflammatory cytokines, UV radiation, bacterial and viral infections. Stimulation triggers the release of NF-kB from IkB in consequence of the phosphorylation and the following degradation of the IkB-alpha protein (P. A. Baeuerle and T. Henkel, Annu. Rev. Immunol. 12: 141–179, 1994). Once it is activated, NF-kB translocates to the nucleus where it binds to DNA at specific kb-sites and induces the transcription of a variety of genes encoding proteins involved in controlling the immune and inflammatory responses, among which a variety of interleukins, the tumor necrosis factor alpha, the NO synthase and the cyclooxigenase 2 (S. Grimm and P. A. Baeuerle, Biochem. J. 290: 297–308, 1993). Accordingly, NF-kB is considered an early mediator of the immune and inflammatory responses and it is involved in the control of cell proliferation and in the pathogenesis of various human diseases, among which rheumatoid arthritis (H. Beker et al., Clin. Exp. Immunol. 99: 325, 1995), ischemia (A. Salminen et al. Biochem. Biophys. Res. Comm. 212: 939, 1995), arteriosclerosis (A. S. Baldwin. Annals Rev. Immunol. 14: 649, 1996), as well as in the pathogenesis of the acquired immunodeficiency syndrome (AIDS), due to the enhanced human immunodeficiency virus (HIV-1) transcription in the presence of activated NF-kB. The increase of HIV-1 virus RNAs transcription by NF-kB is caused by the presence of kb-sites in the (LTR) (Long Terminal Repeats) sequences of the virus genome (M. J. Lenardo and D. Baltimore, Cell 58: 227–229, 1989).

It is also known that prostaglandins (PGs) are a class of naturally occurring cyclic 20-carbon fatty acids that are synthetized by various types of eukaryotic cells in response to external stimuli and play an important role in a variety of physiological responses. Since their discovery, PGs were shown to act as microenvironmental hormones and intracellular signal mediators and to control a large number of physiological and pathological processes, including cell proliferation and differentiation, the immune response, inflammation, cytoprotection and the febrile response. In particular, type A and J PGs, which possess a cyclopentenonic structure, are strong inhibitors of virus replication ("Stress Proteins: Induction and Function" Schlesinger M J, Garaci E., Santoro M. G. ed.s, Springer-Verlag, Heidelberg-Berlin, 2744, 1990). Particularly, it has been recently demonstrated that cyclopentenonic prostaglandins inhibit HIV-1 virus replication, by blocking the viral RNAs transcription (C. Rozera et al. J. Clin. Invest. 97: 1795, 1996).

It is also known that the Heat Shock Proteins (ESPs), also called stress proteins (Proc. Natl. Acad. Sci. USA 86, 8407–8411, 1989), are a family of polypeptides synthetized by eukaryotic and prokaryotic cells in response to heat shock or other kinds of environmental stresses. The HSPs are encoded by a cellular subgroup of genes, identified as stress genes.

The authors have shown that the cyclopentenone prostaglandin PGA inhibits the activation of NF-kB in human cells by inhibiting the phosphorylation and degradation of the inhibitory IkB-alpha protein (A. Rossi, G. Elia and M. G. Santoro, Cold Spring Harbour, N.Y. 1–5 May, 1996, Abstract p. 255).

The authors have also recently shown that inhibition of NF-kB activation is one of the molecular mechanisms used by cyclopentenonic prostaglandins to cause a selective and reversible block of HIV-1 virus RNAs transcription.

SUMMARY OF THE INVENTION

It has now been found that 2-cyclopenten-1-one, the structure constituting the center nucleus of PGA, possesses an activity which is analogous to PGA, that is, it is able to inhibit NF-kB activation, even though it does not contain the corresponding acid function and aliphatic lateral chains. Therefore it is found that the lateral chains, which are present in the PGA with their substituents and double bonds, in particular the acid function, which implies the fatty acid nature of prostaglandins, can be eliminated without substantially modifying the herein above described specific activity. It is also found that the alpha,β-unsaturated carbonyl group in the cyclopentenone ring is the key structure necessary for NF-kB inhibition.

Furthermore it has been found that the inhibition of NF-kB by the cyclopentenone group is related to the ability to activate the HSF transcription factor (Heat Shock Transcription Factor), which is responsible for the synthesis of HSPs (Heat Shock Proteins).

In view of the fact that NF-kB inhibition is associated with HSF activation, it is evident that molecules containing the cyclopentenone nucleus, which is active in inhibiting NF-kB, will be inducers of the HSF factor and therefore they will be inducers of heat shock proteins.

It is therefore an object of the present invention the 2-cyclopenten-1-one, and its substituted derivatives comprising the cyclopentenone nucleus, as inhibitors of NF-kB, the substituents being selected among the ones which do not affect the NF-kB inhibitory activity.

Another object of the present invention is the 2-cyclopenten-1-one and its pharmacologically acceptable derivatives as inhibitors of NF-kB. Another object of the invention is the 2-cyclopenten-1-one and its derivatives as inhibitors of NF-kB with anti-inflammatory, anti-proliferative, immuno-suppressive, cytoprotective and anti-viral activity.

A further object of the invention are pharmaceutical compositions comprising 2-cyclopenten-1-one and/or its pharmaceutically acceptable derivatives to make medicaments with anti-inflammatory, anti-proliferative, immuno-suppressive, cytoprotective antiviral activity. In particular with antiviral activity against the HIV-1 virus and viruses whose transcription is controlled by NF-kB, including herpesviruses.

DETAILED DESCRIPTION OF THE INVENTION

The 2-cyclopenten-1-one is a known product, which can be synthetized according to the process described in Beilstein (Daene, Eder, A. 539 [1939] 207, 211).

According to the present invention 2-cyclopente-1-one, preferably in concentrations ranging between 100 and 500 uM, is able to inhibit NF-kB activation in human cells (FIG. 1A).

Inhibition tests have been carried out in type T lymphoid human cells (Jurkat cell line), as well as in other human cell lines. NF-kB activation was stimulated with 12-o-tetradecanoyl-phorbol-13-acetate (TPA). 2-Cyclopenten-1-one was also effective in inhibiting NF-kB activation after other types of stimulation, including stimulation by tumor necrosis factor alpha or viral infection, and in different types of human cells (data not shown). It is demonstrated that NF-kB inhibition is associated with the activation of HSF factor (FIG. 1B). It is also proved that the ability to inhibit the NF-kB factor is specific for 2-cyclopenten-1-one, whereas similar molecules, such as cyclopentanone and cyclopentene, do not inhibit NF-kB (FIG. 1C) and do not activate HSF (FIG. 1D).

Based on these results it is possible to use 2-cyclopenten-1-one, as well as its pharmaceutically acceptable derivatives, as active substances to produce medicaments, in particular medicaments having activity in inhibiting the NF-kB factor, and in particular:

- anti-inflammatory and immunosuppressive medicaments, in view of the role of NF-kB in stimulating the inflammatory and immune responses;
- cytoprotective medicaments, in view of the role of NF-kB in ischemia and oxidative damages;
- antiproliferative medicaments, in view of the role of NP-kB in cell proliferation;
- antiviral medicaments, in view of the role of NF-kB in activating the viral RNAs transcription.

The following examples are reported to illustrate the invention. They should be considered in any case non limiting the scope of the invention itself.

The reagents used in the examples, including 2-cyclopenten-1-one, cyclopentene, cyclopentanone and 12-o-tetradecanoyl-phorbol-13-acetate (TPA), were products of Sigma Aldrich. $^{32}$P e $^{35}$S were produced by AMERSHAM. Fetal calf serum and cellular culture media were produced by GIBCO.

EXAMPLE 1

Figure 1:
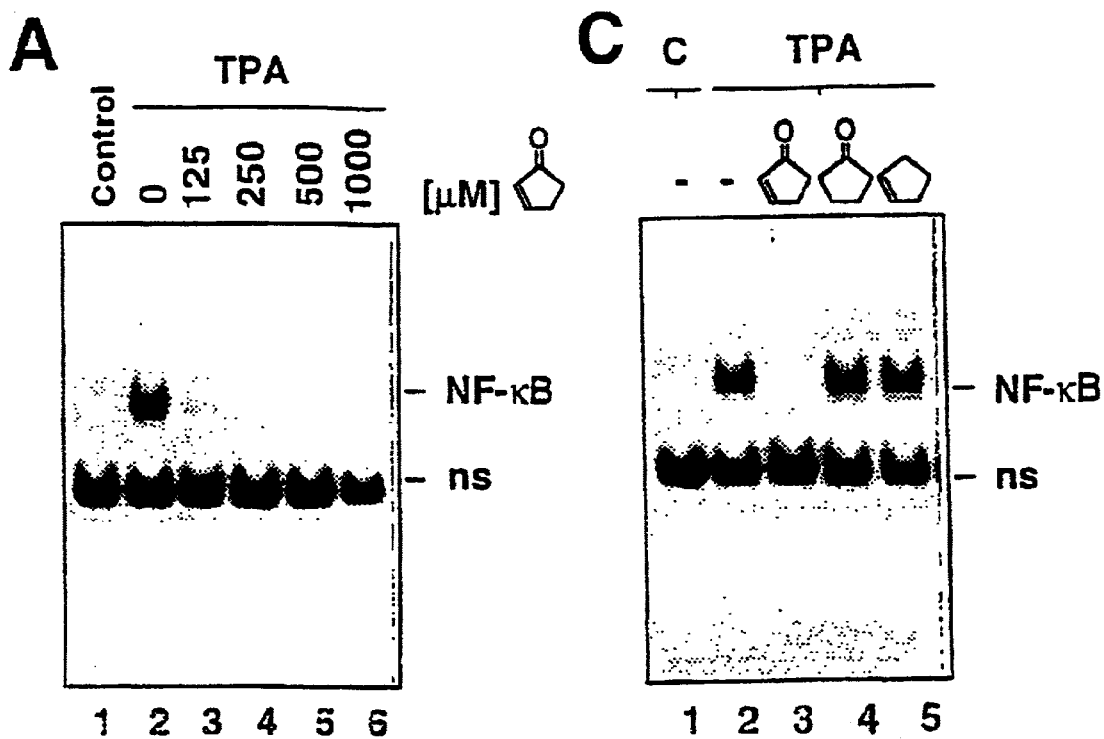
FIG. 1A shows the dose-dependent inhibition of NF-kB activation by 2-cyclopenten-1-one.
FIG. 1B shows the activation of the HSF factor (Heat Shock Transcription Factor) by 2-cyclopenten-1-one in association with NF-kB inhibition.
FIG. 1C shows the specificity of the chemical structure which is responsible for NF-kB inhibition.
FIG. 1D shows the specificity of the chemical structure which is responsible for HSF activation.
Figure 1:
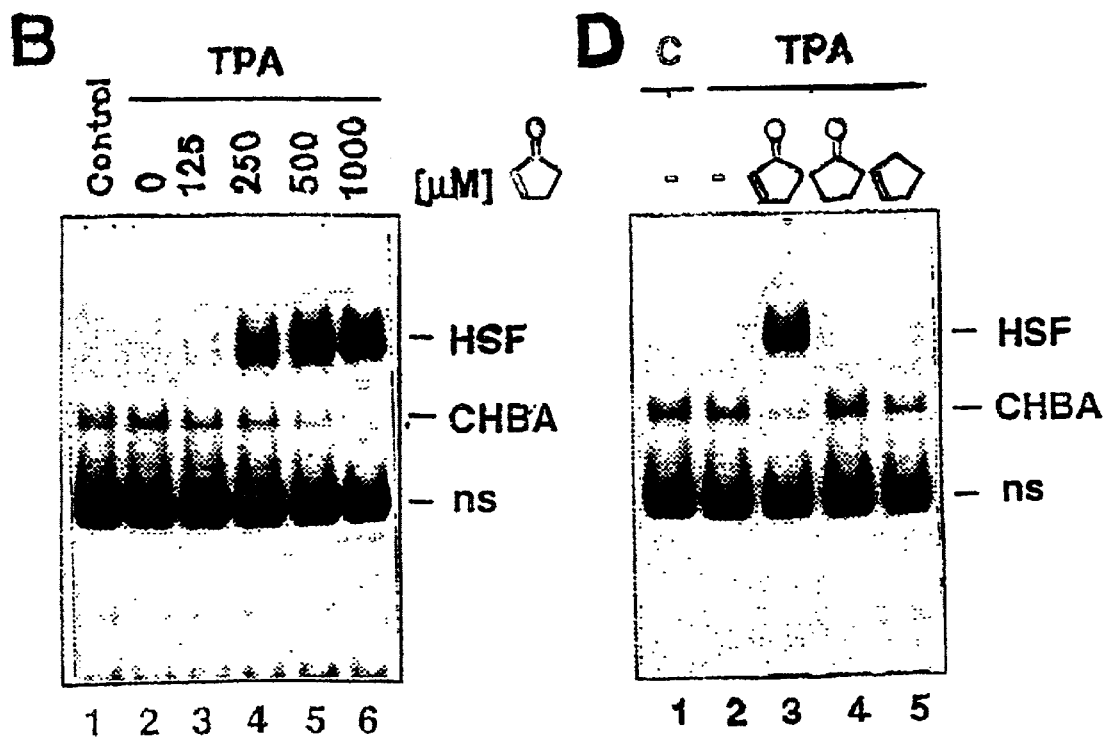

The effect of the treatment with 2-cyclopenten-1-one on NF-kB activation by TPA has been tested in Jurkat cells by using the procedures described hereinbelow and shown in FIG. 1.

Dose-Response Effect

The cells were prepared according to the method described in C. Amici et al. (Cancer Research 55, 4452–4457, 1995).

The cells were treated with 2-cyclopenten-1-one at different concentrations (125–1000 µM) for 1 hour and then were stimulated with TPA (25 ng/ml).

After 3 hours the whole-cell extracts were prepared and subjected to EMSA (Electrophoretic Mobility Shift Assay) as described for NF-kB in U. Zabel et al. (J. Biol. Chem. 266: 242, 1991) and HSF in C. Amici et al. (Cancer Res. 55: 4452, 1995), to determine NF-kB and HSF activation respectively. The positions of the complex NF-kB-DNA (NF-kB) and the non-specific binding (ns) are indicated in FIG. 1A.

The positions of the complex HSF-DNA (HSF), the HSF-DNA constitutive activity (CHBA) and the proteins-DNA non-specific interactions (ns) are indicated in FIG. 1B. The line "econtrol" indicates the non-TPA-stimulated cells as a control of non-activated NF-kB.

As evident, 2-cyclopenten-1-one is able to inhibit NF-kB activation by TPA even at the lower concentration of 125 uM. At the concentration of 500 um the NF-kB band is absent (FIG. A). In correlation with NF-kB inhibition, in the same samples it is evident the activation of HSF starting from the concentration of 125 uM (FIG. 1B).

Specificity of the Inhibitors Effect (FIG. 1C)

The cells were treated for 1 hour with the same concentration (500 uM) of: 2-cyclopenten-1-one (line 3), cyclopentanone (line 4) or cyclopentene (line 5), and then were stimulated with TPA (25 ng/ml). C represents the non-TPA-stimulated control. After 3 hours the whole-cell extracts were prepared and subjected to EMSA to verify the activation of NF-kB (FIG. 1C) and of HSF (FIG. 1D) respectively.

As evident, (i) TPA activates NF-kB (line 2); (ii) 2-cyclopenten-1-one inhibits TPA-induced NF-kB activation (line 3); cyclopentanone (line 4) and cyclopentene (line 5) do not inhibit NF-kB activation.

In addition, as shown in FIG. 1D, in the same samples inhibition of NF-kB, shown in FIG. 1C, is associated with activation of HSF. These results clearly show that the alpha,β-unsaturated carbonyl group is the key structure trigging HSF activation and its presence is necessary to inhibit NF-kB activation.

What is claimed is:

1. A method of treating an inflammatory disorder comprising administering to a subject in which such treatment is needed or desired an amount of 2-cyclopenten-1-one or a pharmaceutically acceptable derivative thereof sufficient to achieve a concentration of 125 to 1000 µM in said subject, wherein said pharmaceutically acceptable derivative is not a cyclopentenone compound having two adjacent aliphatic side chains, or a prostaglandin.

2. The method of claim 1, wherein the concentration of 2-cyclopenten-1-one or a pharmaceutically acceptable derivative thereof is 125 µM, 250 λM, 500 µM or 1000 µM.

3. A method of treating an immune disorder comprising administering to a subject in which such treatment is needed or desired an amount of 2-cyclopenten-1-one or a pharmaceutically acceptable derivative thereof sufficient to achieve a concentration of 125 to 1000 µM in said subject, wherein said pharmaceutically acceptable derivative is not a cyclopentenone compound having two adjacent aliphatic side chains, or a prostaglandin.

4. The method of claim 3, wherein the concentration of 2-cyclopenten-1-one or a pharmaceutically acceptable derivative thereof is 125 µM, 250 µM, 500 µM or 1000 µM.

5. A method of treating a disorder, said disorder involving cell proliferation comprising administering to a subject in which such treatment is needed or desired an amount of 2-cyclopenten-1-one or a pharmaceutically acceptable derivative thereof sufficient to achieve a concentration of 125 to 1000 μM in said subject, wherein said pharmaceutically acceptable derivative is not a cyclopentenone compound having two adjacent aliphatic side chains, or a prostaglandin.

6. The method of claim 5, wherein the concentration of 2-cyclopenten-1-one or a pharmaceutically acceptable derivative thereof is 125 μM, 250 μM, 500 μM or 1000 μM.

7. A method of treating ischemia comprising administering to a subject in which such treatment is needed or desired an amount of 2-cyclopenten-1-one or a pharmaceutically acceptable derivative thereof sufficient to achieve a concentration of 125 to 1000 μM in said subject, wherein said pharmaceutically acceptable derivative is not a cyclopentenone compound having two adjacent aliphatic side chains, or a prostaglandin.

8. The method of claim 7, wherein the concentration of 2-cyclopenten-1-one or a pharmaceutically acceptable derivative thereof is 125 μM, 250 μM, 500 μM or 1000 μM.

9. A method of treating oxidative cell damage comprising administering to a subject in which such treatment is needed or desired an amount of 2-cyclopenten-1-one or a pharmaceutically acceptable derivative thereof sufficient to achieve a concentration of 125 to 1000 μM in said subject, wherein said pharmaceutically acceptable derivative is not a cyclopentenone compound having two adjacent aliphatic side chains, or a prostaglandin.

10. The method of claim 9, wherein the concentration of 2-cyclopenten-1-one or a pharmaceutically acceptable derivative thereof is 125 μM, 250 μM, 500 μM or 1000 μM.

11. A method of treating arteriosclerosis comprising administering to a subject in which such treatment is needed or desired an amount of 2-cyclopenten-1-one or a pharmaceutically acceptable derivative thereof sufficient to achieve a concentration of 125 to 1000 μM in said subject, wherein said pharmaceutically acceptable derivative is not a cyclopentenone compound having two adjacent aliphatic side chains, or a prostaglandin.

12. The method of claim 11, wherein the concentration of 2-cyclopenten-1-one or a pharmaceutically acceptable derivative thereof is 125 μM, 250 μM, 500 μM or 1000 μM.

13. A method of treating rheumatoid arthritis comprising administering to a subject in which such treatment is needed or desired an amount of 2-cyclopenten-1-one or a pharmaceutically acceptable derivative thereof sufficient to achieve a concentration of 125 to 1000 μM in said subject, wherein said pharmaceutically acceptable derivative is not a cyclopentenone compound having two adjacent aliphatic side chains, or a prostaglandin.

14. The method of claim 13, wherein the concentration of 2-cyclopenten-1-one or a pharmaceutically acceptable derivative thereof is 125 μM, 250 μM, 500 μM or 1000 μM.

15. A method of treating a viral infection comprising administering to a subject in which such treatment is needed or desired an amount of 2-cyclopenten-1-one or a pharmaceutically acceptable derivative thereof sufficient to achieve a concentration of 125 to 1000 μM in said subject, wherein said pharmaceutically acceptable derivative is not a cyclopentenone compound having two adjacent aliphatic side chains, or a prostaglandin.

16. The method of claim 15, wherein the concentration of 2-cyclopenten-1-one or a pharmaceutically acceptable derivative thereof is 125 μM, 250 μM, 500 μM or 1000 μM.

17. The method of claim 15, wherein the viral infection an HIV-1 infection.

18. A method of treating a herpes virus infection comprising administering to a subject in which such treatment is needed or desired a therapeutically effective amount of 2-cyclopenten-1-one or a pharmaceutically acceptable derivative thereof, wherein said therapeutically effective amount is effective in inhibiting NF-κB activation and said pharmaceutically acceptable derivative is not a cyclopentenone compound having two adjacent aliphatic side chains, or a prostaglandin.

19. The method of claim 1, wherein the therapeutically effective amount is sufficient to achieve a concentration of 125 to 1000 μM of 2-cyclopenten-1-one or a pharmaceutically acceptable derivative thereof in said subject.

20. The method of claim 18, the therapeutically effective amount is sufficient to achieve a concentration of 125 μM, 250 μM, 500 μM or 1000 μM of 2-cyclopenten-1-one or a pharmaceutically acceptable derivative thereof in said subject.

21. A method of treating AIDS comprising administering to a subject in which such treatment is needed or desired an amount of 2-cyclopenten-1-one or a pharmaceutically acceptable derivative thereof sufficient to achieve a concentration of 125 to 1000 μM in subject, wherein said pharmaceutically acceptable derivative is not a cyclopentenone compound having two adjacent aliphatic side chains, or a prostaglandin.

22. The method of claim 21, wherein the concentration of 2-cyclopenten-1-one or a pharmaceutically acceptable derivative thereof is 125 μM, 250 μM, 500 μM or 1000 μM.

* * * * *

UNITED STATES PATENT AND TRADEMARK OFFICE
CERTIFICATE OF CORRECTION

PATENT NO. : 6,696,498 B2
DATED : February 24, 2004
INVENTOR(S) : Maria Gabriella Santoro, Antonio Rossi and Giuliano Elia It is certified that error appears in the above-identified patent and that said Letters Patent is hereby corrected as shown below:

Column 4,
Line 56, please replace "250λ M" with -- 250µM --

Signed and Sealed this

Twenty-eighth Day of September, 2004

JON W. DUDAS
*Director of the United States Patent and Trademark Office*